US012594058B2

(12) United States Patent
Tadross et al.

(10) Patent No.: US 12,594,058 B2
(45) Date of Patent: Apr. 7, 2026

(54) METHOD AND SYSTEMS FOR COLOR FLOW IMAGING OF ARTERIES AND VEINS

(71) Applicant: GE Precision Healthcare LLC, Waukesha, WI (US)

(72) Inventors: Rimon Tadross, Milwaukee, WI (US); Michael Ledwidge, Westport, WI (US)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 885 days.

(21) Appl. No.: 16/254,460

(22) Filed: Jan. 22, 2019

(65) Prior Publication Data

US 2020/0229795 A1 Jul. 23, 2020

(51) Int. Cl.
| | |
|---|---|
| *A61B 8/00* | (2006.01) |
| *A61B 8/06* | (2006.01) |
| *A61B 8/08* | (2006.01) |

(52) U.S. Cl.
CPC .............. *A61B 8/488* (2013.01); *A61B 8/06* (2013.01); *A61B 8/0891* (2013.01); *A61B 8/468* (2013.01); *A61B 8/469* (2013.01); *A61B 8/5246* (2013.01); *A61B 8/54* (2013.01)

(58) Field of Classification Search
CPC ......... A61B 8/488; A61B 8/06; A61B 8/0891; A61B 8/468; A61B 8/469; A61B 8/5246; A61B 8/54
See application file for complete search history.

(56) References Cited

U.S. PATENT DOCUMENTS

| | | | | |
|---|---|---|---|---|
| 178,935 | A | * 6/1876 | Sokulin | .................. A61K 33/26 424/648 |
| 6,068,598 | A | 5/2000 | Pan et al. | |
| 6,126,605 | A | * 10/2000 | Washburn | ........... G01S 7/52034 600/454 |
| 6,176,830 | B1 | * 1/2001 | Freiburger | .......... G01S 7/52071 600/453 |

(Continued)

FOREIGN PATENT DOCUMENTS

| | | | |
|---|---|---|---|
| CN | 110477955 | A | * 11/2019 |
| CN | 111728643 | A | * 10/2020 |

(Continued)

OTHER PUBLICATIONS

Kruskal et al.: Optimizing Doppler and Color Flow US: Application to Hepatic Sonography. RadioGraphics. 2004 (Year: 2004).*

(Continued)

*Primary Examiner* — Christopher Koharski
*Assistant Examiner* — Helene Bor
(74) *Attorney, Agent, or Firm* — McCoy Russell LLP

(57) ABSTRACT

Various methods and systems for color flow ultrasound imaging of arteries and veins are provided. In one embodiment, a method comprises acquiring a color flow image, automatically identifying an artery and a vein within the color flow image, and adjusting at least one imaging parameter responsive to the automatic identification of the artery and the vein. In this way, flow velocities and volume flow in arteries and veins may be measured with minimal adjustments or input by a user, thereby increasing the accuracy and consistency of measurements and reducing the time needed for blood flow measurements.

21 Claims, 7 Drawing Sheets

(56)                    References Cited

U.S. PATENT DOCUMENTS

| | | | | |
|---|---|---|---|---|
| 6,192,264 | B1 * | 2/2001 | Foo | A61B 5/055 |
| | | | | 324/309 |
| 6,464,641 | B1 * | 10/2002 | Pan | A61B 8/06 |
| | | | | 600/453 |
| 10,945,678 | B2 * | 3/2021 | Oka | A61B 5/7275 |
| 2014/0213905 | A1 * | 7/2014 | Saad | A61B 8/06 |
| | | | | 600/441 |
| 2014/0343431 | A1 * | 11/2014 | Vajinepalli | A61B 8/468 |
| | | | | 600/454 |
| 2017/0252004 | A1 * | 9/2017 | Broad | A61B 8/145 |
| 2018/0344262 | A1 * | 12/2018 | Oka | A61B 5/742 |
| 2019/0099161 | A1 * | 4/2019 | Faraggi | A61B 8/5207 |
| 2019/0298304 | A1 * | 10/2019 | Igarashi | G06T 7/246 |
| 2020/0129144 | A1 * | 4/2020 | Rajguru | A61B 8/463 |

FOREIGN PATENT DOCUMENTS

| | | | | | |
|---|---|---|---|---|---|
| EP | 1152364 | B1 * | 9/2007 | | A61B 5/1075 |
| WO | WO-0027288 | A1 * | 5/2000 | | A61B 8/06 |
| WO | WO-2006122001 | A2 * | 11/2006 | | A61B 34/20 |
| WO | WO-2019234164 | A1 * | 12/2019 | | A61B 8/488 |

OTHER PUBLICATIONS

Rubin et al. ("Questions an Answers—Aliasing") (Year: 1992).*

* cited by examiner

METHOD AND SYSTEMS FOR COLOR FLOW IMAGING OF ARTERIES AND VEINS

FIELD

Embodiments of the subject matter disclosed herein relate to ultrasound imaging.

BACKGROUND

Medical diagnostic ultrasound imaging systems typically include a set of imaging modes, such as a B mode and color flow Doppler mode. For B-mode imaging, the ultrasound imaging system generates a two-dimensional image of tissue in which the brightness of a pixel corresponds to the intensity of the echo return. Alternatively, in a color flow imaging mode, the Doppler effect is used to detect the presence of blood flow in the body. Flow velocities in a given location in a vessel can be estimated using the measured Doppler shift and correcting for the Doppler angle between the ultrasound beams and the vessel orientation.

BRIEF DESCRIPTION

In one embodiment, a method comprises acquiring a color flow image, automatically identifying an artery and a vein within the color flow image, and adjusting at least one imaging parameter responsive to the automatic identification of the artery and the vein. In this way, flow velocities and volume flow in arteries and veins may be measured with minimal adjustments or input by a user, thereby increasing the accuracy and consistency of measurements and reducing the time needed for blood flow measurements.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
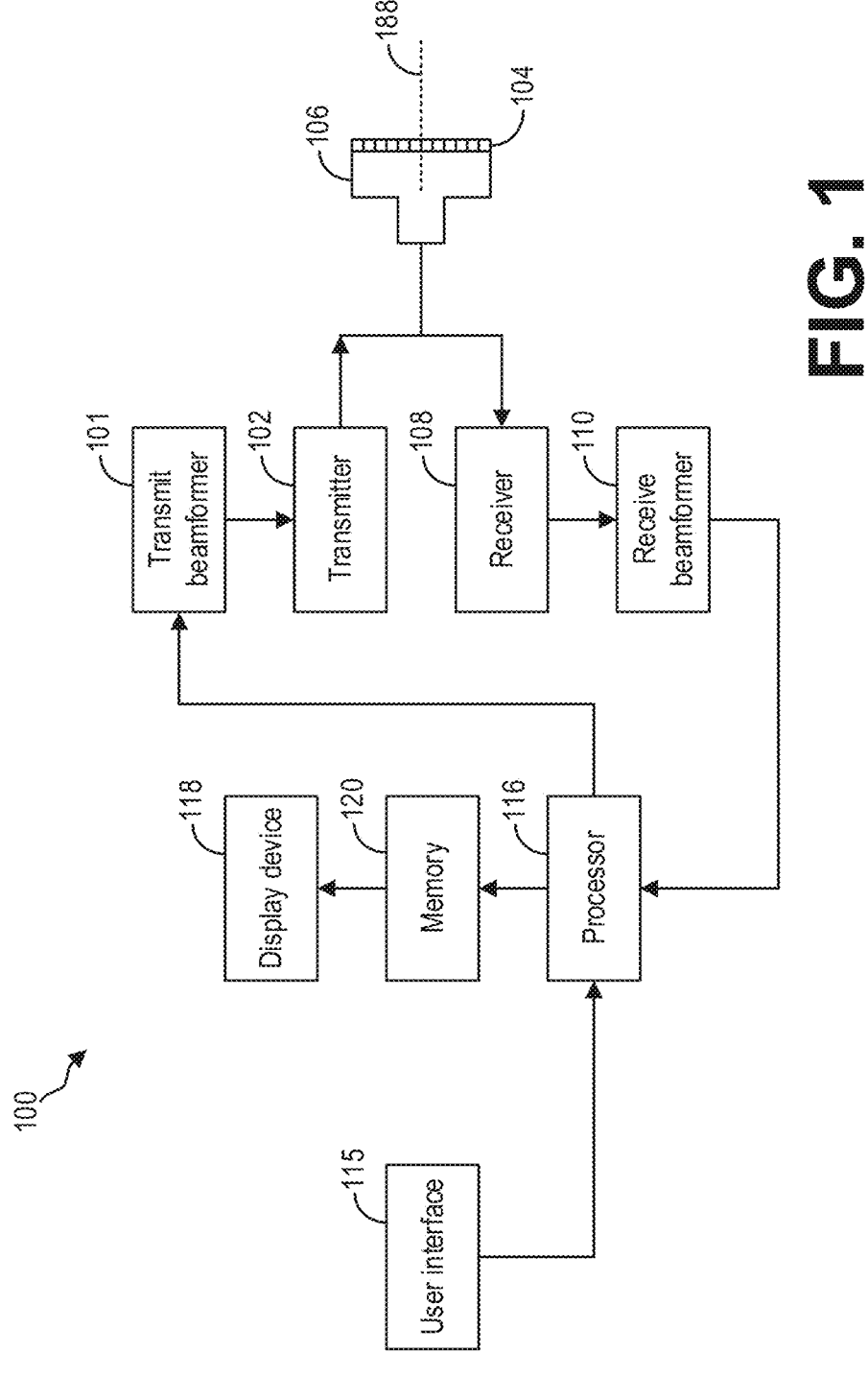
FIG. 1 shows an example ultrasound imaging system according to an embodiment.

The following description relates to various embodiments of ultrasound imaging using an ultrasound imaging system, such as the ultrasound imaging system shown in FIG. 1. In particular, systems and methods for color flow or Doppler imaging of arteries and veins are provided. Previous approaches to color flow imaging typically require an operator of the ultrasound imaging system to manually identify the vessels in a color flow image, and to manually adjust a position of a pulsed wave cursor to align with the vessels. The pulsed wave cursor in turn controls various color flow imaging parameters, such as the steering angle, the Doppler angle, and the Doppler sample gate position. Such manual approaches are susceptible to error, and furthermore become time consuming when fine angle adjustments are necessary. A method for color flow imaging of arteries and veins, such as the method depicted in FIG. 2, includes automatically identifying an artery and a vein in a color flow image, and adjusting imaging parameters such as steering angle and Doppler angle accordingly. Some techniques for color flow imaging of arteries and veins include initially segmenting a color flow image into different vessels to aid the positioning of the pulsed wave cursor. However, if an artery and a vein are adjacent to each other in the color flow image, the segmentation technique may not accurately segment the two vessels. Relying solely on the segmentation technique, the pulsed wave cursor may be erroneously positioned between the artery and the vein, leading to inaccurate measurements of flow velocities and flow volumes. To avoid such inaccuracies, a method for color flow imaging of arteries and veins, such as the method depicted in FIG. 3, may include explicitly discriminating between the artery and the vein when both are present in a segmented region of a color flow image. The method for distinguishing the artery from the vein depends on the selected color flow imaging application. For example, if a venous imaging application is selected, the pulse repetition frequency of the color flow beam may be low, and so a method for distinguishing the artery from the vein, such as the method depicted in FIG. 4, includes detecting aliasing caused by the arterial blood flow which is relatively higher than the sampling rate or pulse repetition frequency. In contrast, if an arterial application is selected, the pulse repetition frequency is higher than for venous applications, and so aliasing does not occur. Therefore, a method for distinguishing the artery from the vein, such as the method depicted in FIG. 5, includes detecting flow directions, and recognizing that the blood flow in an artery is opposite to the blood flow of an adjacent vein. Alternatively, a method for distinguishing the artery from the vein in arterial imaging applications, such as the method depicted in FIG. 6, includes measuring pulsatility in the color flow image, and recognizing that arteries exhibit pulsatile flow whereas veins do not. As depicted in FIGS. 7-11, the pulsed wave cursor and/or the color flow region of interest may be automatically adjusted according to the distinguishing of the artery from the vein.

FIG. 1 is a schematic diagram of an ultrasound imaging system 100 in accordance with an embodiment. The ultrasound imaging system 100 includes a transmit beamformer 101 and a transmitter 102 that drive elements 104 within a transducer array, or ultrasound probe, 106 to emit pulsed ultrasonic signals into a body (not shown). The ultrasound probe 106 may, for instance, comprise a linear array probe, a curvilinear array probe, a sector probe, or any other type of ultrasound probe configured to acquire both two-dimensional (2D) B-mode data and 2D color flow data or both 2D B-mode data and another ultrasound mode that detects blood flow velocity in the direction of a vessel axis. The elements 104 of the ultrasound probe 106 may therefore be arranged in a one-dimensional (1D) or 2D array. Still referring to FIG. 1, the pulsed ultrasonic signals are back-scattered from structures in the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. According to some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be situated within the ultrasound probe 106. The terms "scan" or "scanning" may also be used in this disclosure to refer to acquiring data through the process of transmitting and receiving ultrasonic signals. The term "data" and "ultrasound data" may be used in this disclosure to refer to one or more datasets acquired with an ultrasound imaging system.

A user interface 115 may be used to control operation of the ultrasound imaging system 100, including, to control the input of patient data, to change a scanning or display parameter, to select various modes, operations, and parameters, and the like. The user interface 115 may include one or more of a rotary, a mouse, a keyboard, a trackball, hard keys linked to specific actions, soft keys that may be configured to control different functions, a graphical user interface displayed on the display device 118 in embodiments wherein display device 118 comprises a touch-sensitive display device or touch screen, and the like. In some examples, the user interface 115 may include a proximity sensor configured to detect objects or gestures that are within several centimeters of the proximity sensor. The proximity sensor may be located on either the display device 118 or as part of a touch screen. The user interface 115 may include a touch screen positioned in front of the display device 118, for example, or the touch screen may be separate from the display device 118. The user interface 115 may also include one or more physical controls such as buttons, sliders, rotary knobs, keyboards, mice, trackballs, and so on, either alone or in combination with graphical user interface icons displayed on the display device 118. The display device 118 may be configured to display a graphical user interface (GUI) from instructions stored in memory 120. The GUI may include user interface icons to represent commands and instructions. The user interface icons of the GUI are configured so that a user may select commands associated with each specific user interface icon in order to initiate various functions controlled by the GUI. For example, various user interface icons may be used to represent windows, menus, buttons, cursors, scroll bars, and so on. According to embodiments where the user interface 115 includes a touch screen, the touch screen may be configured to interact with the GUI displayed on the display device 118. The touch screen may be a single-touch touch screen that is configured to detect a single contact point at a time or the touch screen may be a multi-touch touch screen that is configured to detect multiple points of contact at a time. For embodiments where the touch screen is a multi-point touch screen, the touch screen may be configured to detect multi-touch gestures involving contact from two or more of a user's fingers at a time. The touch screen may be a resistive touch screen, a capacitive touch screen, or any other type of touch screen that is configured to receive inputs from a stylus or one or more of a user's fingers. According to other embodiments, the touch screen may comprise an optical touch screen that uses technology such as infrared light or other frequencies of light to detect one or more points of contact initiated by a user.

According to various embodiments, the user interface 115 may include an off-the-shelf consumer electronic device such as a smartphone, a tablet, a laptop, and so on. For the purposes of this disclosure, the term "off-the-shelf consumer electronic device" is defined to be an electronic device that was designed and developed for general consumer use and one that was not specifically designed for use in a medical environment. According to some embodiments, the consumer electronic device may be physically separate from the rest of the ultrasound imaging system 100. The consumer electronic device may communicate with the processor 116 through a wireless protocol, such as Wi-Fi, Bluetooth, Wireless Local Area Network (WLAN), near-field communication, and so on. According to an embodiment, the consumer electronic device may communicate with the processor 116 through an open Application Programming Interface (API).

The ultrasound imaging system 100 also includes a processor 116 to control the transmit beamformer 101, the transmitter 102, the receiver 108, and the receive beamformer 110. The processor 116 is configured to receive inputs from the user interface 115. The receive beamformer 110 may comprise either a conventional hardware beamformer or a software beamformer according to various embodiments. If the receive beamformer 110 is a software beamformer, the receive beamformer 110 may comprise one or more of a graphics processing unit (GPU), a microprocessor, a central processing unit (CPU), a digital signal processor (DSP), or any other type of processor capable of performing logical operations. The receive beamformer 110 may be configured to perform conventional beamforming techniques as well as techniques such as retrospective transmit beamforming (RTB). If the receive beamformer 110 is a software beamformer, the processor 116 may be configured to perform some or all of the functions associated with the receive beamformer 110.

The processor 116 is in electronic communication with the ultrasound probe 106. For purposes of this disclosure, the term "electronic communication" may be defined to include both wired and wireless communications. The processor 116 may control the ultrasound probe 106 to acquire data. The processor 116 controls which of the elements 104 are active and the shape of a beam emitted from the ultrasound probe 106. The processor 116 is also in electronic communication with a display device 118, and the processor 116 may process the data into images for display on the display device 118. The processor 116 may include a CPU according to an embodiment. According to other embodiments, the processor 116 may include other electronic components capable of carrying out processing functions, such as a GPU, a microprocessor, a DSP, a field-programmable gate array (FPGA), or any other type of processor capable of performing logical operations. According to other embodiments, the processor 116 may include multiple electronic components capable of carrying out processing functions. For example, the processor 116 may include two or more electronic components selected from a list of electronic components including: a CPU, a DSP, an FPGA, and a GPU. According to another embodiment, the processor 116 may also include a complex demodulator (not shown) that demodulates the RF data and generates raw data. In another embodiment the demodulation can be carried out earlier in the processing chain. The processor 116 is adapted to perform one or more processing operations according to a plurality of selectable ultrasound modalities on the data. The data may be processed in real-time during a scanning session as the echo signals are received. For the purposes of this disclosure, the term "real-time" is defined to include a procedure that is performed without any intentional delay. For example, an embodiment may acquire images at a real-time rate of 7-20 volumes/sec. The ultrasound imaging system 100 may acquire 2D data of one or more planes at a significantly faster rate. However, it should be understood that the real-time volume-rate may be dependent on the length of time that it takes to acquire each volume of data for display. Accordingly, when acquiring a relatively large volume of data, the real-time volume-rate may be slower. Thus, some embodiments may have real-time volume-rates that are considerably faster than 20 volumes/sec while other embodiments may have real-time volume-rates slower than 7 volumes/sec. The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data prior to displaying an image. It should be appreciated that other embodiments may use a different arrangement of processors.

The ultrasound imaging system 100 may continuously acquire data at a volume-rate of, for example, 10 Hz to 30 Hz. Images generated from the data may be refreshed at a similar frame-rate. Other embodiments may acquire and display data at different rates. For example, some embodiments may acquire data at a volume-rate of less than 10 Hz or greater than 30 Hz depending on the size of the volume and the intended application. The memory 120 is included for storing processed volumes of acquired data. In an exemplary embodiment, the memory 120 is of sufficient capacity to store at least several seconds worth of volumes of ultrasound data. The volumes of data are stored in a manner to facilitate retrieval thereof according to its order or time of acquisition. The memory 120 may comprise any known data storage medium.

Optionally, embodiments of the present invention may be implemented utilizing contrast agents. Contrast imaging generates enhanced images of anatomical structures and blood flow in a body when using ultrasound contrast agents including microbubbles. After acquiring data while using a contrast agent, the image analysis includes separating harmonic and linear components, enhancing the harmonic component and generating an ultrasound image by utilizing the enhanced harmonic component. Separation of harmonic components from the received signals is performed using suitable filters. The use of contrast agents for ultrasound imaging is well-known by those skilled in the art and will therefore not be described in further detail.

In various embodiments of the present invention, data may be processed by other or different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. The image lines and/or volumes are stored and timing information indicating a time at which the data was acquired in memory may be recorded. The modules may include, for example, a scan conversion module to perform scan conversion operations to convert the image volumes from beam space coordinates to display space coordinates. A video processor module may be provided that reads the image volumes from a memory and displays an image in real time while a procedure is being carried out on a patient. A video processor module may store the images in an image memory, from which the images are read and displayed.

As mentioned above, the ultrasound probe 106 may comprise a linear probe or a curved array probe. FIG. 1 further depicts a longitudinal axis 188 of the ultrasound probe 106. The longitudinal axis 188 of the ultrasound probe 106 extends through and is parallel to a handle of the ultrasound probe 106. Further, the longitudinal axis 188 of the ultrasound probe 106 is perpendicular to an array face of the elements 104.

Figure 2:
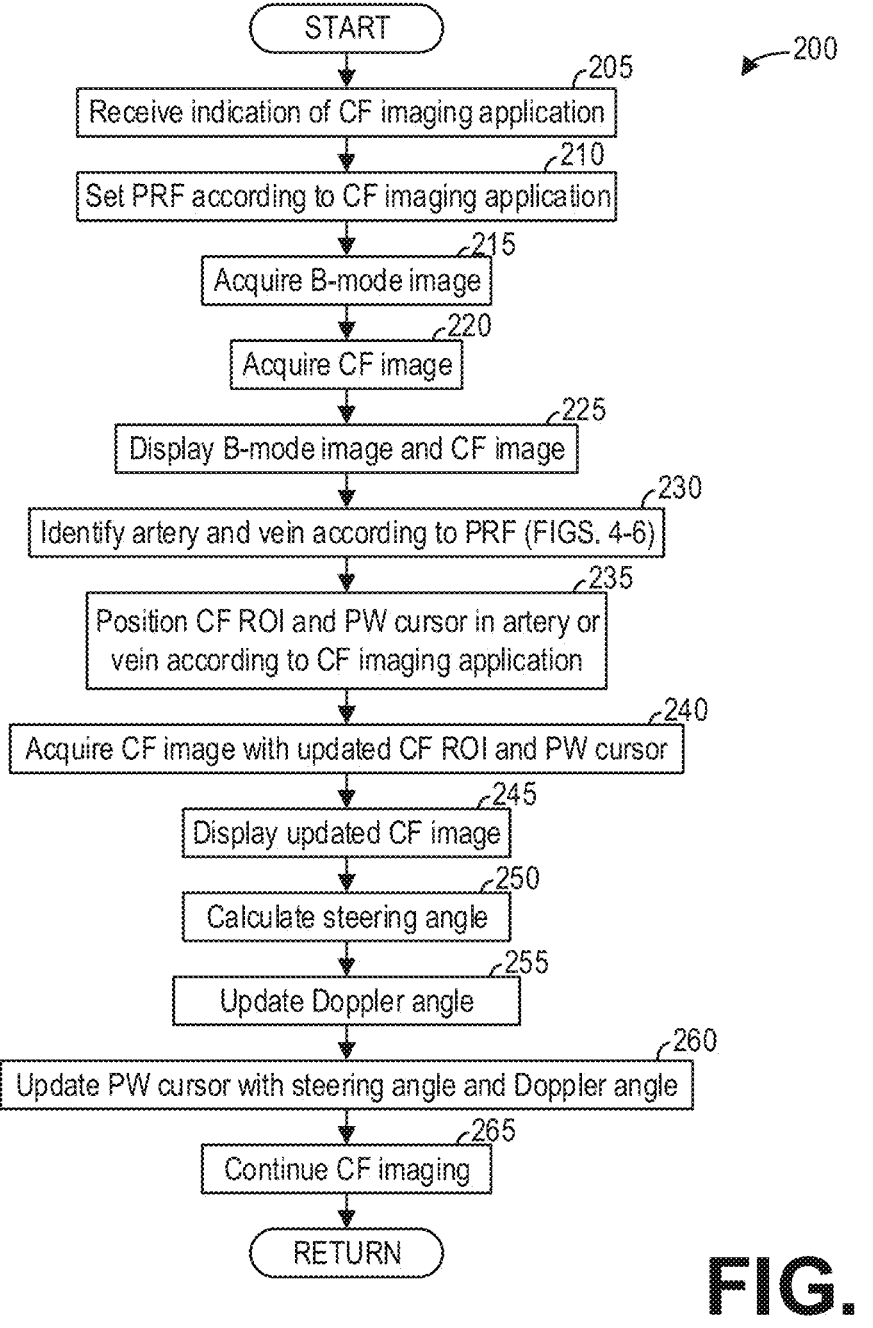
FIG. 2 shows a high-level flow chart illustrating an example method for color flow imaging according to an embodiment.

FIG. 2 shows a high-level flow chart illustrating an example method 200 for color flow (CF) imaging according to an embodiment. In particular, method 200 relates to robust identification of arteries and veins in a CF image and automatically steering and positioning a CF region of interest (ROI) and a pulsed wave (PW) cursor relative to the identified arteries and veins during CF imaging. Method 200 is described with regard to the systems and components of FIG. 1, though it should be appreciated that the method 200 may be implemented with other systems and components without departing from the scope of the present disclosure. Method 200 may be implemented, for example, as executable instructions in non-transitory memory, such as memory 120, of an ultrasound imaging system, such as ultrasound imaging system 100, and executable by a processor, such as processor 116.

Method 200 begins at 205. At 205, method 200 receives an indication of a color flow (CF) imaging application. For example, an operator of the ultrasound imaging system 100 may input, via the user interface 115, a selection of a CF imaging application. The selected CF imaging application may comprise a venous imaging application or an arterial imaging application. A venous imaging application, for example, may be directed to imaging veins and thus an indication of a venous imaging application may prescribe one or more parameters for optimally imaging veins. Similarly, an arterial imaging application may be directed to imaging arteries and thus an indication of an arterial imaging application prescribes one or more parameters for optimally imaging arteries.

As an example, continuing at 210, method 200 sets the pulse repetition frequency (PRF) for the CF imaging according to the selected CF imaging application. The PRF comprises the number of pulses occurring in one second, for example, and the PRF may be adjusted according to characteristics of the subject being imaged. For example, if the CF imaging application indicated at 205 comprises a venous imaging application, the PRF may be set to a first PRF comprising a relatively low value in order to detect the slow venous blood flow. In contrast, if the CF imaging application comprises an arterial imaging application, the PRF may be set to a second PRF relatively higher than the first PRF as arterial blood flow may be substantially higher than venous blood flow given the increased blood pressure of arteries with respect to the blood pressure of veins. In this way, the PRF comprises a sampling frequency of the CF imaging.

At 215, method 200 acquires a B-mode image. For example, method 200 controls the transmit beamformer 101 and transmitter 102 to drive the elements 104 of the ultrasound probe 106 to emit ultrasonic pulses into the subject, and further controls the receiver 108 and receive beamformer 110 to process echoes of the ultrasonic pulses reflected by structures in the subject and received by the elements 104 of the ultrasound probe 106. The echoes are processed to form the B-mode (or brightness mode) image, a cross-sectional image representing tissues and organ boundaries with the body, wherein each echo is displayed at a point in the image which corresponds to the relative position of the echo's origin within the body cross section, and wherein the brightness of the image at each point is related to the strength or amplitude of the corresponding echo.

Further, at 220, method 200 acquires a CF image. To acquire the CF image, method 200 controls the transmit beamformer 101 and the transmitter 102 to drive the elements 104 of the ultrasound probe 106 to emit a series of pulses at the PRF set at 210 into the subject, and further controls the receiver 108 and receive beamformer 110 to process echoes of the series of ultrasonic pulses reflected by moving objects (i.e., flowing blood) within the subject and received by the elements 104 of the ultrasound probe 106. As noted above with regard to the B-mode image, the echoes from stationary tissue are the mostly the same from pulse to pulse and so the structures discerned in the B-mode image are similarly stationary. In contrast, echoes from moving scatterers such as blood exhibit slight differences in the time for the echo signal to return to the ultrasound probe 106. Such time differences are measured to derive the Doppler frequency and processed to generate the CF image. In particular, the phase shift of backscattered pulses is used to measure the velocity of the backscatterers from blood. It should be appreciated that while tissue imaged in the B-mode image may not necessarily be stationary, filters may be employed in the transmit and receive components of the ultrasound imaging system 100 to filter out high amplitude, low-frequency Doppler signals resulting from tissue movement due to vessel wall motion, for example.

The CF image thus formed visualizes the Doppler shift corresponding to flow velocities of blood rather than physical structures. The flow velocities may be visualized in the CF image, for example, by different colors and/or shades of colors. For example, flow towards the ultrasound probe 106 may be depicted in red while flow away from the ultrasound probe 106 may be depicted in blue, with varying shades of red and blue to indicate varying velocity levels.

At 225, method 200 displays the B-mode image and the CF image. For example, method 200 may display the CF image superimposed over the B-mode image via the display device 118. Further, it should be appreciated that in some examples, method 200 acquires the B-mode image and the CF image simultaneously, while in other examples, method 200 acquires the B-mode image and the CF image sequentially.

At 230, method 200 identifies one or more arteries and one or more veins according to CF imaging application, and specifically based on the PRF set at 210. For example, if the selected CF imaging application comprises a venous imaging application, and thus the PRF comprises the first PRF to detect the slow venous blood flow, method 200 identifies arteries within the CF image by identifying structures within the CF image that exhibit high variance in flow velocities. That is, as the flow velocities for an artery are likely above the sampling rate set by the first PRF, aliasing occurs wherein the vessel appears to have flow going in different directions, such as occurs when there is turbulent flow. In contrast, the first PRF is specifically set to image venous blood flow, and so structures exhibiting low variance or non-turbulent blood flow in a single direction are identified as vein(s). Method 200 thus distinguishes arteries from veins for venous imaging applications by identifying structures with aliasing as arteries. As another example, when the CF imaging application comprises an arterial imaging application and the PRF is set to the second PRF higher than the first PRF for imaging arterial flow, aliasing does not occur because the PRF is sufficiently high enough to image the relatively faster arterial flow. Instead, the direction of the flow may be used to distinguish between arteries and veins. In another example, for arterial imaging applications, method 200 may distinguish arteries from veins according to pulsatility. Pulsatility comprises a measure of pulsatile flow or a flow with periodic variations, generally associated with blood flow in arteries. That is, arteries typically exhibit pulsatile flow whereas veins do not exhibit pulsatile flow. Therefore, method 200 may distinguish an artery from a vein according to measured pulsatility of different structures in the CF image. Particular methods for identifying arteries and veins in the CF image are described further herein with regard to FIGS. 4-6.

At 235, method 200 positions a CF region of interest (ROI) and a pulsed wave (PW) cursor in the artery or the vein according to the selected CF imaging application. Specifically, method 200 centers the CF ROI and the PW cursor on the artery if the selected CF imaging application comprises an arterial imaging application, or on the vein if the selected CF imaging application comprises a venous imaging application. The CF ROI establishes the CF field of view for CF imaging. Further, the PW cursor comprises a set of graphics corresponding to CF imaging parameters which may be displayed or superimposed on the ultrasound image comprising the B-mode image and the CF image. The PW cursor includes a Doppler beam cursor corresponding to the CF or Doppler beam centerline and a vessel slope cursor corresponding to the orientation of the vessel walls or the flow direction of the blood within the vessel (i.e., the flow axis). An angle between the Doppler beam cursor and the vessel slope cursor comprises the Doppler angle which is used to convert Doppler frequency shifts into velocity units according to the Doppler equation. The PW cursor further includes a Doppler range gate indicating a sample volume, wherein the blood velocity is specifically calculated by measuring the phase shift from firing to firing within the Doppler range gate. The size of the Doppler range gate is visualized in the PW cursor by the distance between a top and bottom graphic, or otherwise by a geometry of the Doppler range gate (e.g., with a circle).

To position the CF ROI and the PW cursor in the artery or the vein according to the selected CF imaging application, method 200 centers the CF ROI and the PW cursor on a selected point within the vein or the artery for a venous or arterial imaging application, respectively. Method 200 may specifically center the Doppler range gate of the PW cursor on the selected point with the vein or the artery.

After automatically updating the position of the CF ROI and the PW cursor to align with the vessel of interest (i.e., the artery or the vein) at 235, method 200 continues to 240. At 240, method 200 acquires a CF image with the updated CF ROI and PW cursor, and at 245, method 200 displays the updated CF image via the display device 118. The updated CF image may be superimposed or overlaid on the B-mode image acquired at 215, for example, or method 200 may additionally acquire an updated B-mode image for display with the updated CF image.

Continuing at 250, method 200 calculates or selects a steering angle. The steering angle comprises the angle between the CF beam and the longitudinal axis 188 of the ultrasound probe 106, for example. Method 200 selects a steering angle to steer the CF beam and thus minimize the Doppler angle. Further, at 255, method 200 updates the Doppler angle by adjusting the vessel slope cursor to accurately align with the flow axis, and then updating the Doppler angle between the adjusted vessel slope and the selected steering angle.

At 260, method 200 updates the PW cursor with the steering angle and the Doppler angle. For example, method 200 may display the updated PW cursor with the selected steering angle and the updated Doppler angle. Method 200 may accordingly update the CF imaging parameters corresponding to the PW cursor. Continuing at 265, method 200 continues CF imaging with the updated CF imaging parameters. For example, method 200 acquires additional CF images with a CF beam steered with the steering angle, and measures Doppler shifts according to the updated Doppler angle. Method 200 then returns.

It should be appreciated that while FIG. 2 depicts the automatic positioning and automatic steering in sequence, both the positioning of the CF ROI and the PW cursor as well as adjustments to the steering angle and/or Doppler angle may be performed simultaneously to reduce the time for improved imaging. For example, at 235, method 200 may further perform the actions of 250 and 255 (i.e., adjusting the steering angle and Doppler angle) while positioning the CF ROI and PW cursor in the artery or vein, such that the automated steering and positioning is based off of the single CF image acquired at 220. The steering angle and/or Doppler angle may be further automatically adjusted at 250 and 255, respectively, as depicted, according to the updated CF image acquired at 240, though in some examples such additional steering may not be necessary.

Figure 3:
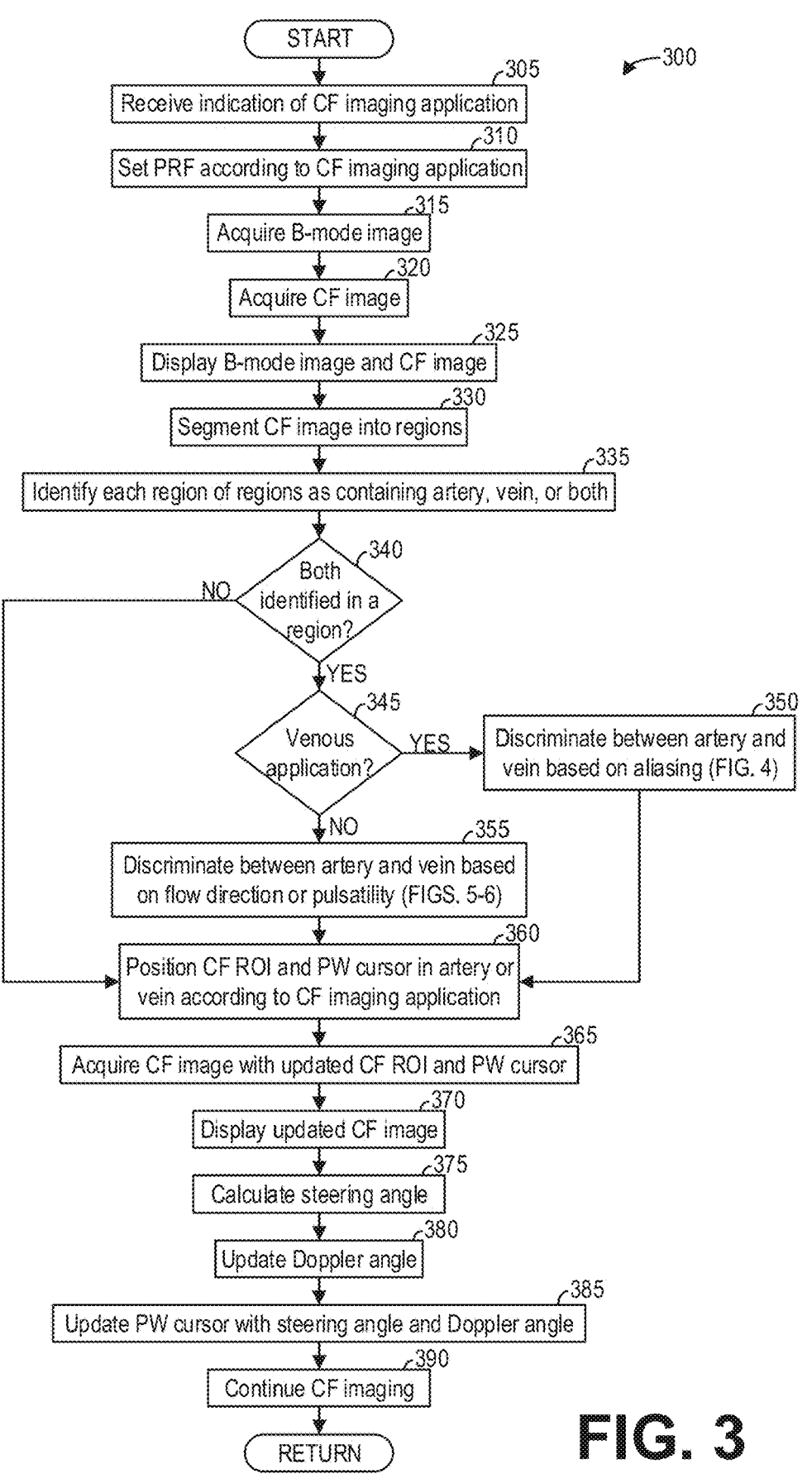
FIG. 3 shows a high-level flow chart illustrating another example method for color flow imaging according to an embodiment.

FIG. 3 shows a high-level flow chart illustrating another example method 300 for color flow (CF) imaging according to an embodiment. In particular, method 300 relates to robust identification of arteries and veins in a CF image when both an artery and a vein are present in a segmented region of a CF image. Method 300 is described with regard to the systems and components of FIG. 1, though it should be appreciated that the method 300 may be implemented with other systems and components without departing from the scope of the present disclosure. Method 300 may be implemented, for example, as executable instructions in non-transitory memory, such as memory 120, of an ultrasound imaging system, such as ultrasound imaging system 100, and executable by a processor, such as processor 116.

Method 300 begins at 305. At 305, method 300 receives an indication of a color flow (CF) imaging application. For example, an operator of the ultrasound imaging system 100 may input, via the user interface 115, a selection of a CF imaging application. The selected CF imaging application may indicate a venous imaging application or an arterial imaging application. Continuing at 310, method 300 sets the PRF according to the selected CF imaging application. For example, method 300 sets the PRF to the first, low PRF described hereinabove for a venous imaging application, and to a second PRF higher than the first PRF for an arterial imaging application.

Continuing at 315, method 300 acquires a B-mode image, and at 320, method 300 acquires a CF image. Method 300 may simultaneously or sequentially acquire the B-mode image and the CF image. At 325, method 300 displays an ultrasound image comprising the B-mode image and the CF image. The CF image is displayed over the B-mode image, for example, via the display device 118. The methods at 305, 310, 315, 320, and 325 may proceed similarly to the methods described above at 205, 210, 215, 220, and 225, respectively.

At 330, method 300 segments the CF image into regions. For example, method 300 may segment different vessels or structures present within the CF image into different regions. For example, method 300 may partition the CF image into regions such that each distinct structure within the CF image is positioned within a region. At 335, method 300 identifies each region of the segmented regions as containing an artery, a vein, or both. For example, method 300 may employ a vessel segment search method to identify vessels within the CF image and/or the B-mode image according to geometric and morphological information. More specifically, method 300 may evaluate vessel segments or structures within the CF image according to vessel diameter, vessel length or area, uniformity of diameter, or a combination of such measures. Method 300 may distinguish between arteries and veins within the regions according to such measures. However, if a vein and artery are touching or in contact in the CF image, method 300 may not be able to properly distinguish the vein and artery from each other according to the vessel segment search because of the shared diameter of the vessels. The vein and artery in contact may thus be segmented into a same region.

At 340, method 300 determines if both an artery and a vein are identified in a same region. Alternatively, method 300 may determine if a region is not positively identified as an artery or a vein, which thereby may suggest that the region includes both an artery and a vein. If an artery and a vein are not identified in a same region ("NO"), method 300 proceeds to 360. However, if an artery and a vein are both identified in a region ("YES"), method 300 proceeds to 345.

The technique for distinguishing the artery and the vein from each other within a shared region may differ according to the selected CF imaging application. Therefore, at 345, method 300 determines if the CF imaging application is a venous imaging application. If the CF imaging application is a venous imaging application ("YES"), method 300 continues to 350. At 350, method 300 discriminates between the artery and the vein based on aliasing. For example, method 300 may discriminate between the artery and the vein by identifying aliasing in the region, for example by scanning the region with the first PRF, and labeling the aliasing portion of the region as an artery. Such a method for discriminating between the artery and the vein based on the first PRF is described further herein with regard to FIG. 4. After discriminating between the artery and the vein based on the first PRF, method 300 continues to 360.

However, referring again to 345, if the CF imaging application is an arterial imaging application instead of a venous imaging application ("NO"), method 300 continues to 365. At 365, method 300 discriminates between the artery and the vein based on flow direction or pulsatility. For example, method 300 may distinguish the artery from the vein within the region according to the flow direction of each vessel, or alternatively based on pulsatility of the vessels. Such methods for discriminating between the artery and the vein based on the second PRF is described further herein with regard to FIGS. 5 and 6. After discriminating between the artery and the vein based on the second PRF, method 300 continues to 360.

At 360, method 300 positions the CF ROI and the PW cursor in the artery or the vein according to the CF imaging application. For example, as discussed hereinabove with regard to FIG. 2, method 300 centers the CF ROI and the PW cursor on the artery or the vein according to whether the CF imaging application is an arterial imaging application or a venous imaging application, respectively. At 365, method 300 acquires a CF image with the updated CF ROI and the PW cursor, and method 300 displays the updated CF image via the display device 118 at 370.

Continuing at 375, method 300 calculates or selects a steering angle to minimize the Doppler angle, and then at 380, method 300 updates the Doppler angle. At 385, method 300 updates the PW cursor with the steering angle and the Doppler angle. At 390, method 300 continues CF imaging with the updated PW cursor. Method 300 then returns. Method 300 may be executed again during a single CF imaging session responsive to detecting the position of the ultrasound probe 106 changing, for example based on significant updates to positions of structures in the B-mode images.

Thus, methods and systems are provided for automatic color flow beam steering and automatic adjustments of a color flow or pulsed wave cursor with respect to a vessel of interest. The term "automatic" as used herein refers to actions being performed by a processor of the ultrasound imaging system 100, such as processor 116, rather than by a human operator of the ultrasound imaging system 100. Thus, according to the methods provided herein, the operator of the ultrasound imaging system 100 may select, via the user interface 115, a desired imaging application to indicate whether an artery or a vein is the vessel of interest in a color flow imaging session. The ultrasound imaging system 100 then automatically identifies the artery and vein within a color flow image and automatically positions the PW cursor and the CF ROI relative to the artery or the vein, without user input from the operator. That is, the operator of the ultrasound imaging system 100 does not input an indication of where the artery and the vein are located within the color flow image. Further, the operator of the ultrasound imaging system 100 does not input the position of the CF ROI, the PW cursor, or adjustments to the steering angle or the Doppler angle, for the methods described herein.

Figure 4:
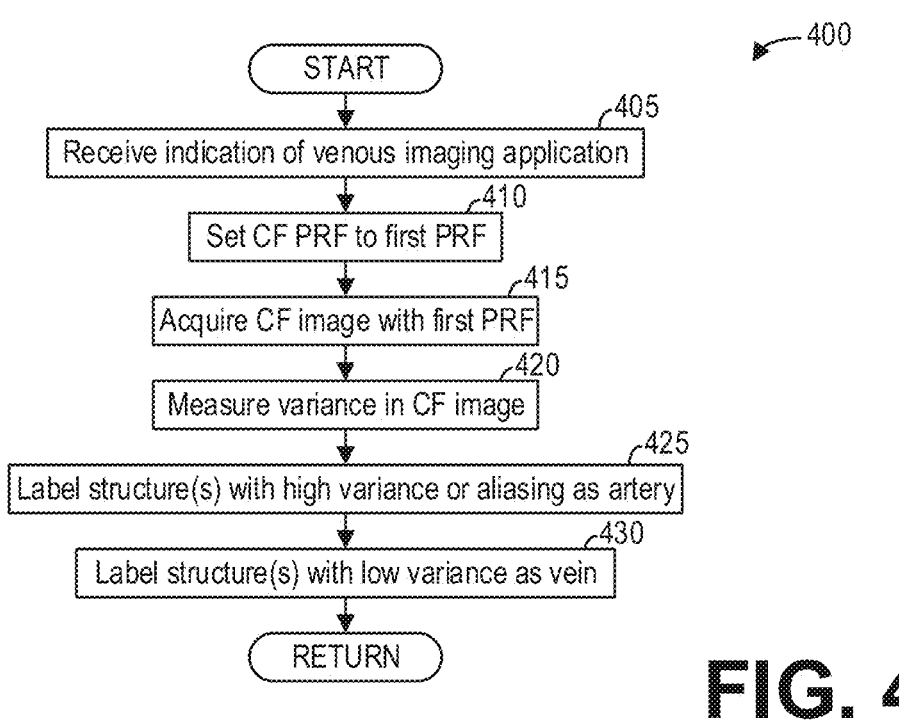
FIG. 4 shows a high-level flow chart illustrating an example method for discriminating between arteries and veins based on velocity variance according to an embodiment.
Figure 5:
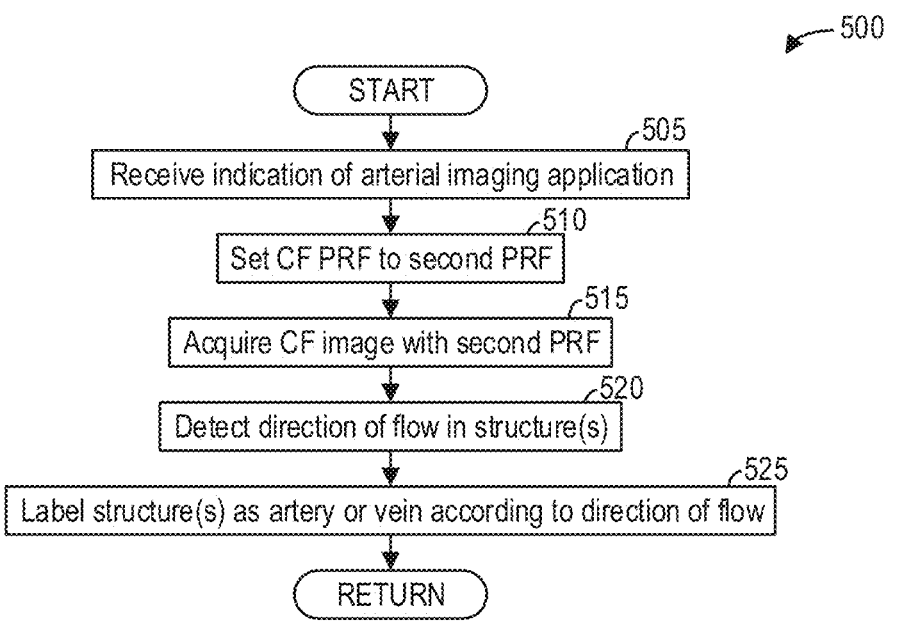
FIG. 5 shows a high-level flow chart illustrating an example method for discriminating between arteries and veins based on flow direction according to an embodiment.
Figure 6:
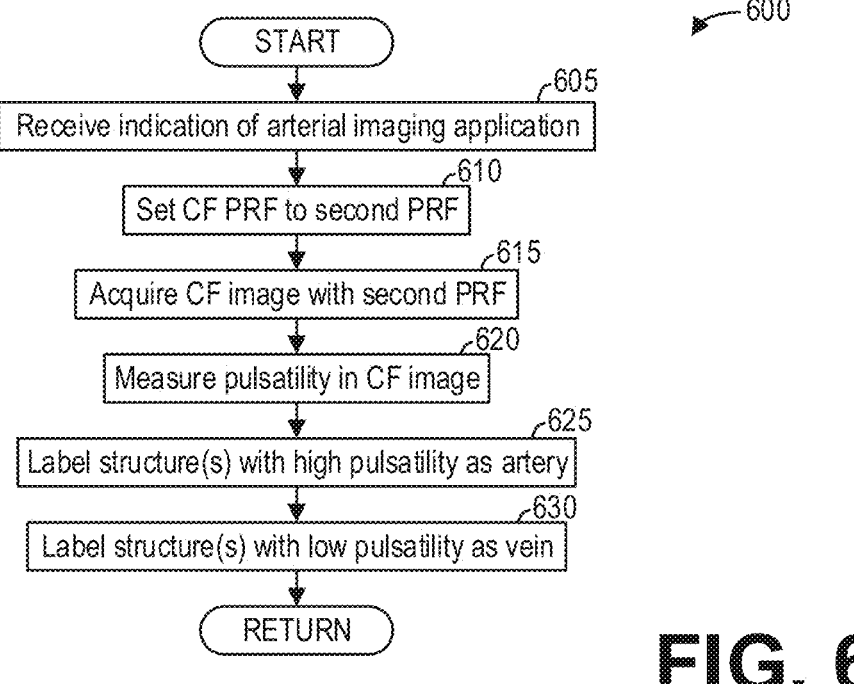
FIG. 6 shows a high-level flow chart illustrating an example method for discriminating between arteries and veins based on pulsatility according to an embodiment.

As mentioned above, various methods by which the ultrasound imaging system 100 may automatically identify the artery and the vein within a color flow image are provided herein and described further with regard to FIGS. 4-6.

FIG. 4 shows a high-level flow chart illustrating an example method 400 for distinguishing an artery from a vein in a CF image for a venous imaging application according to an embodiment. In particular, method 400 relates to accurately identifying arteries and veins within a CF image for venous imaging applications, such that the accuracy of automatic steering and PW cursor positioning for CF imaging, as discussed hereinabove with regard to FIGS. 2 and 3, may be improved. Method 400 is described with regard to the systems, components, and methods of FIGS. 1-3, though it should be understood that method 400 may be implemented with other systems, components, and methods without departing from the scope of the present disclosure. As an illustrative and non-limiting example, method 400 may be implemented as executable instructions in non-transitory memory, such as memory 120, of an ultrasound imaging system, such as ultrasound imaging system 100, may be executable by a processor, such as processor 116, as a sub-routine of method 200 or 300.

Method 400 begins at 405. At 405, method 400 includes receiving an indication of a venous imaging application. Responsive to receiving the indication of the venous imaging application, at 410, method 400 sets the CF PRF to the first PRF. As discussed hereinabove, the first PRF comprises a low PRF suitable for imaging venous blood flow. Continuing at 415, method 400 acquires a CF image with the first PRF. In some examples, method 400 may control the transmit beamformer 101 and the transmitter 102 to drive the elements 104 of the ultrasound transducer 106 to generate ultrasonic pulses with the first PRF, and to further control the receiver 108 and the receive beamformer 110 to process echoes of the ultrasonic pulses received with the elements 104 to form the CF image. Alternatively, when method 400 comprises a sub-routine of method 200 or method 300, for example, method 400 may import the CF image acquired at 220 or 320, respectively. Additionally, in some examples, with regard to method 300, method 400 may import the segmented region including both the artery and the vein in contact with each other.

Continuing at 420, method 400 measures the variance in flow velocities or Doppler shifts of the CF image. As the low value of the first PRF is configured to detect the slow venous blood flow, the variance in regions corresponding to an artery will be high, whereas the variance in regions corresponding to a vein will be relatively low. In particular, the variance in regions corresponding to an artery will suggest turbulent flow, as aliasing causes the variance in flow velocities. That is, flow velocities which are high relative to the PRF may be exhibit spatial and/or temporal variance in velocity, and specifically direction, thereby resulting in aliasing in regions of arterial blood flow. For example, spatial variance may be indicated by a plurality of objects (i.e., blood) clustered together in a region of the CF image with varying speeds of flow and directions of flow, whereas temporal variance may be indicated by velocities varying within a region over time (e.g., across CF images or frames acquired in sequence). Such spatial and temporal variance may be a consequence of the relatively low sample rate or PRF causing aliasing in regions corresponding to arterial blood flow.

Therefore, at 425, method 400 labels one or more structure(s) in the CF image with high variance or aliasing as an artery. Further, at 430, method 400 labels one or more structure(s) with low variance as a vein. The labeled structures may then be output such that the CF ROI and PW cursor may be accordingly positioned relative to the labeled structures, as discussed hereinabove with regard to FIGS. 2 and 3. Method 400 then returns.

Thus, a method for distinguishing an artery from a vein for venous CF imaging applications includes identifying the artery and the vein in a CF image according to local spatial velocity variance or direction change, or temporal velocity variance or direction change. Further, as an alternative or in addition to labeling the identified structures, method 400 may separate the artery and the vein into independent segments or regions.

FIG. 5 shows a high-level flow chart illustrating an example method 500 for identifying structures in CF images as an artery or a vein for arterial imaging applications according to an embodiment. In particular, method 500 relates to distinguishing an artery from a vein for arterial imaging applications based on the direction of blood flow, such that the accuracy of automatic steering and PW cursor positioning for CF imaging, as discussed hereinabove with regard to FIGS. 2 and 3, may be improved. Method 500 is described with regard to the systems, components, and methods of FIGS. 1-3, though it should be understood that method 500 may be implemented with other systems, components, and methods without departing from the scope of the present disclosure. As an illustrative and non-limiting example, method 500 may be implemented as executable instructions in non-transitory memory, such as memory 120, of an ultrasound imaging system, such as ultrasound imaging system 100, may be executable by a processor, such as processor 116, as a sub-routine of method 200 or 300.

Method 500 begins at 505. At 505, method 500 receives an indication of an arterial imaging application. Responsive to receiving the indication of an arterial imaging application, at 510, method 500 sets the CF PRF to a second PRF optimized for imaging arterial blood flow. The second PRF is higher than the first PRF discussed hereinabove with regard to venous imaging applications.

At 515, method 500 acquires a CF image with the second PRF. In some examples, method 500 may control the transmit beamformer 101 and the transmitter 102 to drive the elements 104 of the ultrasound transducer 106 to generate ultrasonic pulses with the second PRF, and to further control the receiver 108 and the receive beamformer 110 to process echoes of the ultrasonic pulses received with the elements 104 to form the CF image. Alternatively, when method 500 comprises a sub-routine of method 200 or method 300, for example, method 500 may import the CF image acquired at 220 or 320, respectively. Additionally, in some examples, with regard to method 300, method 500 may import the segmented region including both the artery and the vein in contact with each other.

Continuing at 520, method 500 detects the direction of flow in one or more structure(s). For an artery and a vein positioned adjacent to each other, the blood flow in each vessel runs opposite to the other vessel. Thus, in the CF image acquired at 515, the direction of flow for each vessel should be discernable due to the higher PRF. For example, one vessel may be blue in the CF image whereas the other vessel may be red, thereby indicating opposing flow directions.

At 525, method 500 labels the structures as an artery or a vein according to the direction of flow within the structure. To label the structures as an artery or a vein according to the direction of flow, method 500 may segment the structures into different segments, and may identify the segments as the artery or vein using the vessel segment search (e.g., according to the vessel diameter, vessel area, uniformity of vessel diameter, or a combination of such measures as discussed hereinabove). As another example, method 500 may detect the position of the ultrasound probe 106 based on the relative position of anatomical structures in the B-mode image. The indication of the arterial imaging application may further indicate which artery is being imaged, for example. Method 500 may therefore determine, according to the particular artery being imaged and the orientation of the ultrasound probe 106 relative to the artery, which vessel comprises a vein and which vessel comprises the artery according to the blood flow direction. To that end, method 500 may reference a look-up table of relative blood flow directions for arteries and veins for different arterial imaging applications, as an illustrative example. Method 500 then returns.

FIG. 6 shows a high-level flow chart illustrating an example method 600 for identifying structures in a CF image as an artery or a vein for an arterial imaging application according to an embodiment. In particular, method 600 relates to distinguishing an artery from a vein in a CF image based on measured pulsatility, such that the accuracy of automatic steering and PW cursor positioning for CF imaging, as discussed hereinabove with regard to FIGS. 2 and 3, may be improved. Method 600 is described with regard to the systems, components, and methods of FIGS. 1-3, though it should be understood that method 600 may be implemented with other systems, components, and methods without departing from the scope of the present disclosure. As an illustrative and non-limiting example, method 600 may be implemented as executable instructions in non-transitory memory, such as memory 120, of an ultrasound imaging system, such as ultrasound imaging system 100, may be executable by a processor, such as processor 116, as a sub-routine of method 200 or 300.

Method 600 begins at 605. At 605, method 600 receives an indication of an arterial imaging application. Responsive to receiving the indication of the arterial imaging application, at 610, method 600 sets the CF PRF to the second PRF optimized for imaging arterial blood flow.

At 615, method 600 acquires a CF image with the second PRF. In some examples, method 600 may control the transmit beamformer 101 and the transmitter 102 to drive the elements 104 of the ultrasound transducer 106 to generate ultrasonic pulses with the second PRF, and to further control the receiver 108 and the receive beamformer 110 to process echoes of the ultrasonic pulses received with the elements 104 to form the CF image. Alternatively, when method 600 comprises a sub-routine of method 200 or method 300, for example, method 600 may import the CF image acquired at 220 or 320, respectively. Additionally, in some examples, with regard to method 300, method 600 may import the segmented region including both the artery and the vein in contact with each other.

At 620, method 600 measures pulsatility in the CF image. Arteries exhibit pulsatile flow whereas veins do not exhibit pulsatile flow. Therefore, at 625, method 600 labels structure(s) in the CF image with high pulsatility as an artery. At 630, method 600 labels structure(s) in the CF image with low pulsatility or no pulsatility as a vein. Method 600 then returns. The labeled structures may thus be used as described hereinabove with regard to FIGS. 2 and 3 to for automatic steering and automatic positioning of the CF ROI and PW cursor.

Figure 7:
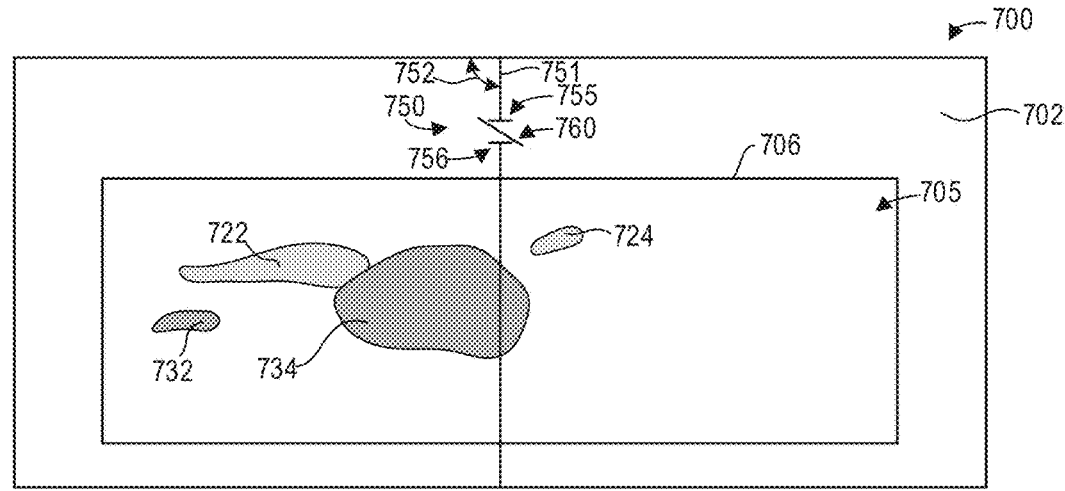
FIG. 7 shows an example ultrasound image including a B-mode image and a color flow image in an initial state according to an embodiment.

FIG. 7 shows an example ultrasound image 700 including a B-mode image 702 and a color flow image 705 in an initial state according to an embodiment. As depicted, the CF image 705 is superimposed over the B-mode image 702. In the initial state after initial acquisition of the B-mode image 702 and the CF image 705, the CF ROI 706 is in a default or initial position and orientation relative to the B-mode image 702. Further, the PW cursor 750 is in an initial or default position. As depicted, the PW cursor 750 includes a Doppler beam cursor 751 indicating the CF or Doppler beam centerline, an upper Doppler gate graphic 755 and a lower Doppler gate graphic 756 indicating a Doppler range gate or sample volume, and a vessel slope cursor 760 indicating the flow axis. As the PW cursor 750 is in the initial state, the steering angle 752 between the CW centerline indicated by the Doppler beam cursor 751 and the direction of the B-mode imaging plane is in an initial state (e.g., 90 degrees).

Multiple structures including a first structure 722, a second structure 724, a third structure 732, and a fourth structure 734 indicated by Doppler shifts are present within the CF image 705. As depicted by the different gray levels, the blood flow in the first structure 722 and the second structure 724 is flowing in a direction opposite to the direction of flow in the third structure 732 and the fourth structure 734. It should be appreciated that the gray scale is presented for simplicity, and that different color schemes, such as red and blue, may be used to indicate different directions of Doppler shifts.

For an arterial imaging application, for example, the method 500 described hereinabove may be able to distinguish the structures from each other according to the opposing blood flow directions clearly visible in the CF image 705. Further, the fourth structure 734 may be identified as corresponding to an artery based on an estimation of the vessel diameter, for example. The method 500 when applied to the CF image 705 may therefore label the third and fourth structures 732 and 734 as corresponding to the artery, and further labels the first and second structures 722 and 724 as corresponding to a vein.

Figure 8:
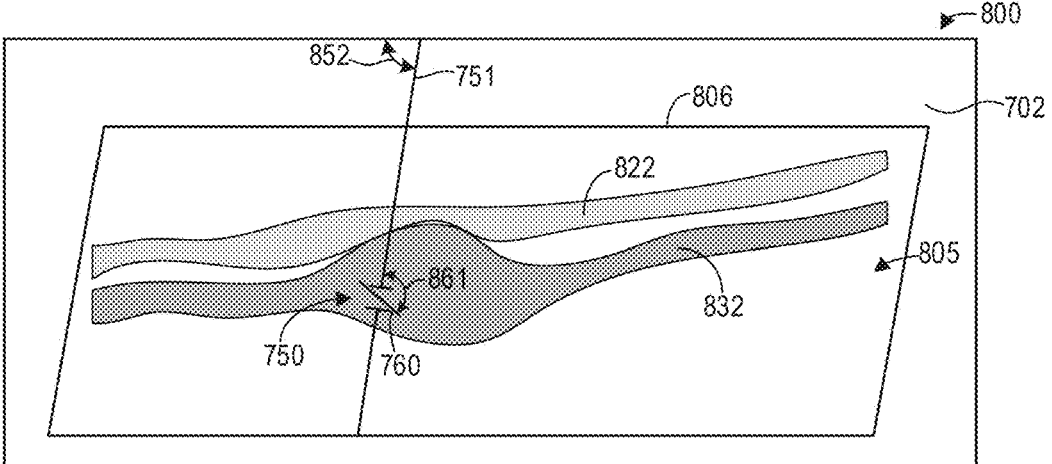
FIG. 8 shows an example ultrasound image including a B-mode image and an updated color flow image with a pulsed wave cursor automatically positioned on an artery according to an embodiment.

With regard to method 200 of FIG. 2, for example, the method 200 automatically adjusts the position of the CF ROI 706 and/or the PW cursor 750 with respect to the position of the structure 734. As an illustrative example, FIG. 8 shows an example ultrasound image 800 including the B-mode image 702 and an updated color flow image 805 with the PW cursor 750 automatically positioned on an artery 832 according to an embodiment. That is, after positioning the PW cursor 750 on the fourth structure 734 identified as an artery, the initial steering angle 752 may be adjusted to another steering angle 852, also reflected in the orientation of the CF ROI 806. Specifically, the range gate indicated by the upper and lower Doppler gate graphics 755 and 756 are automatically positioned within the fourth structure 734. The resulting CF image 805, acquired after selecting the steering angle 852 and positioning the Doppler gate range on the fourth structure 734, includes a more complete image of the vein indicated by the first structure 822 and a more complete image of the artery indicated by the second structure 832. The Doppler angle 861 between the vessel slope cursor 760 and the Doppler beam cursor 751 is still in the default angle.

Figure 9:
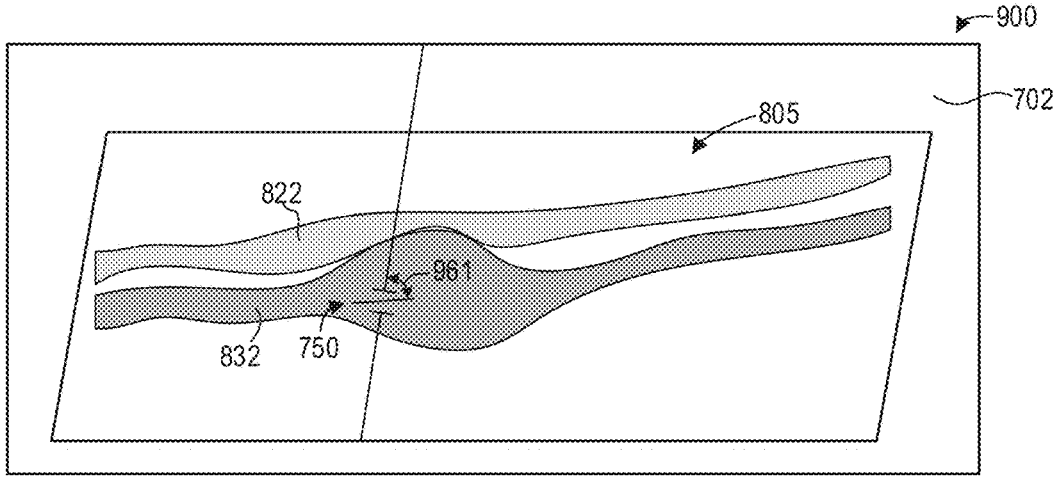
FIG. 9 shows the example ultrasound image of FIG. 8 with an automatically updated Doppler angle according to an embodiment.

After acquiring the more complete visualization of the artery with the second structure 832, the vessel slope corresponding to the flow axis may be automatically updated. For example, FIG. 9 shows an example ultrasound image 900 comprising the B-mode image 702 and the updated CF image 805 of FIG. 8 with an automatically updated Doppler angle 961. The Doppler angle 961 is automatically aligned with the flow of the second structure 832 or the artery. Consequently, accurate flow velocities may be calculated or measured from the Doppler shifts depicted in the CF image 805 with the automatically updated Doppler angle 961.

By automatically positioning the PW cursor 750 on the desired structure, automatically selecting the steering angle 852 to optimize possible Doppler angles, and automatically adjusting the orientation of the vessel slope cursor 760 to align with the flow axis and thus obtain the optimized Doppler angle 961, flow velocities and flow volumes of the artery may be accurately obtained with minimal user input. Further, as the correct positioning and aligning of the various cursor elements may be error-prone and time-consuming when performed manually by an operator of the ultrasound imaging system, the time for obtaining accurate flow velocities and flow volumes is reduced by the methods and systems described herein, as the methods described herein do not require any user input with regard to the position of the PW cursor 750 or any cursor elements thereof. Further, the consistency and accuracy of blood flow measurements across a plurality of color flow imaging sessions is improved, as the accuracy of blood flow measurements does not depend on the experience or efficiency of the operator. That is, as a processor such as the processor 116 of an ultrasound imaging system such as the ultrasound imaging system 100 is configured to automatically distinguish an artery from a vein in a color flow image, center the PW cursor and/or the color flow region of interest on the artery or vein depending on the imaging application, adjust the steering angle, and adjust the Doppler angle, the accuracy and consistency of blood flow measurements is substantially improved relative to the accuracy and consistency of blood flow measurements obtained via manual control by a human operator, and furthermore the time necessary for obtaining such accurate and consistent blood flow measurements is substantially reduced relative to the amount of time a human operator would take to obtain such accurate and consistent blood flow measurements.

Figure 10:
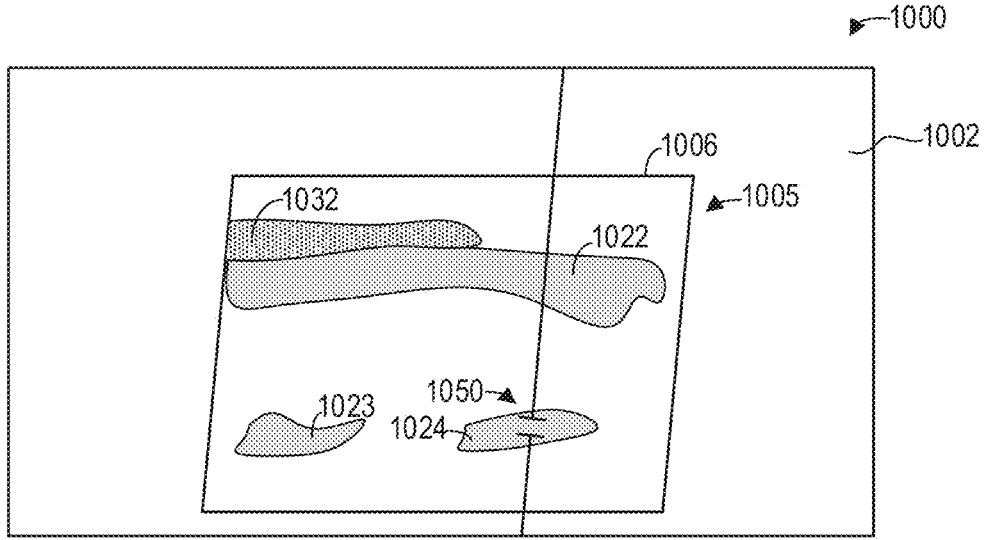
FIG. 10 shows an example ultrasound image including a B-mode image and a color flow image in an initial state according to an embodiment.

As another illustrative example, FIG. 10 shows an example ultrasound image 1000 including a B-mode image 1002 and a CF image 1005 in an initial state according to an embodiment. As depicted, the CF image 1005 includes a first structure 1022, a second structure 1023, and a third structure 1024 within the CF ROI 1006. The PW cursor 1050 is initially positioned over the third structure 1024. For a venous imaging application, the vessel segment search may identify the first structure 1022 as most likely corresponding to a vein in the CF image 1005. However, such a vessel segment search may erroneously identify the first structure 1022 and a fourth structure 1032 partially overlapping the first structure 1022 as a single structure. Without accurately distinguishing the two structures, the PW cursor 1050 may be erroneously centered between the first structure 1022 and the fourth structure 1032. Measurements of flow velocity and other CF imaging measurements may be inaccurate as a consequence.

To properly distinguish the first structure 1022 from the fourth structure 1032, the variance in Doppler shifts or flow velocities may be measured throughout the CF image 1005. The fourth structure 1032 may subsequently exhibit high variance or aliasing, suggesting turbulent flow in both directions, whereas the first structure 1022 may indicate low variance, or flow in a single direction throughout the structure. The two structures may thus be distinguished from each other, and the first structure 1022 may be accurately identified as the vein according to the low variance as well as results of a vessel segment search performed on the properly distinguished structures.

Figure 11:
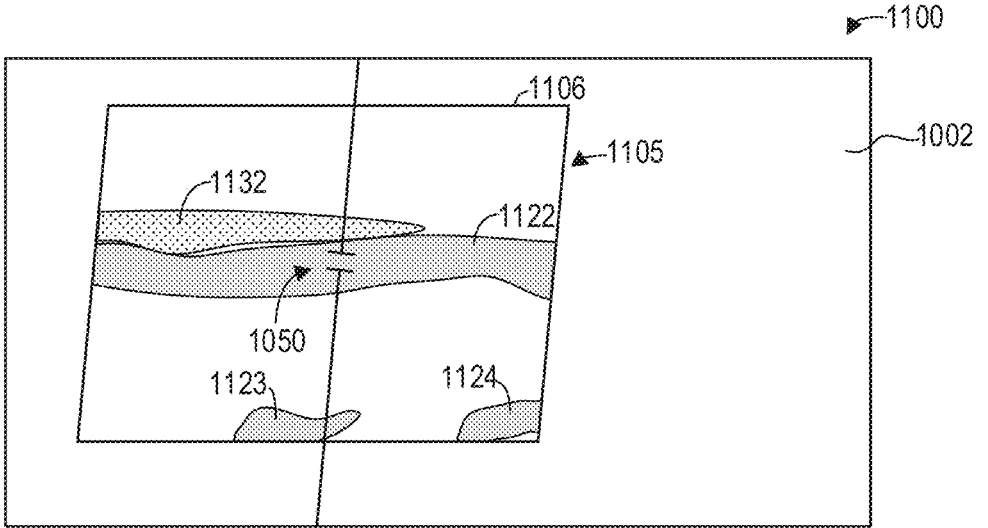
FIG. 11 shows an example ultrasound image including a B-mode image and an updated color flow image with a pulsed wave cursor automatically positioned on a vein according to an embodiment.

FIG. 11 shows an example ultrasound image 1100 including the B-mode image 1002 and an updated CF image 1104 with the PW cursor 1050 automatically positioned on the vein 1122 corresponding to the first structure 1022 of FIG. 11. In addition to the PW cursor 1050, the CF ROI 1106 is centered on the vein 1122. The updated CF image 1104 includes the vein 1122 as well as the artery corresponding to the fourth structure 1032. Additional venous structures 1123 and 1124 are also depicted, which correspond to the second and third structures 1023 and 1024 of FIG. 11.

Thus, methods and systems are provided for accurate color flow imaging of arteries and veins. A technical effect of the disclosure includes the improved automatic steering for color flow imaging. Another technical effect of the disclosure includes improved measurements of flow velocities in arteries and veins during color flow imaging. Yet another technical effect of the disclosure includes the display of a pulsed wave cursor automatically positioned within a vein or artery despite the vein or artery in face-sharing contact with another blood vessel.

In one embodiment, a method comprises acquiring a color flow image, automatically identifying an artery and a vein within the color flow image, and adjusting at least one imaging parameter responsive to the automatic identification of the artery and the vein.

In a first example of the method, the method further comprises receiving an selection of a venous imaging application or an arterial imaging application, wherein acquiring the color flow image comprises scanning a subject with a first pulse repetition frequency or a second pulse repetition frequency according to the selection of the venous imaging application or the arterial imaging application, respectively, the second pulse repetition frequency higher than the first pulse repetition frequency. In a second example of the method optionally including the first example, automatically identifying the artery and the vein within the color flow image comprises, responsive to receiving the selection of the venous imaging application and acquiring the color flow image with the first pulse repetition frequency, measuring, with a processor, variance in flow velocities within the color flow image, labeling, with the processor, a first structure with a high variance as the artery, and labeling, with the processor, a second structure with a low variance as the vein. In a third example of the method optionally including one or more of the first and second examples, automatically identifying the artery and the vein within the color flow image comprises, responsive to receiving the selection of the arterial imaging application and acquiring the color flow image with the second pulse repetition frequency, identifying, with a processor, a first structure with a first flow direction and a second structure with a second flow direction opposite the first flow direction in the color flow image, and labeling, with the processor, the first structure and the second structure respectively as the artery and the vein. In a fourth example of the method optionally including one or more of the first through third examples, automatically identifying the artery and the vein within the color flow image comprises, responsive to receiving the selection of the arterial imaging application and acquiring the color flow image with the second pulse repetition frequency, measuring, with a processor, pulsatility in the color flow image, identifying, with the processor, a first structure with a high pulsatility as the artery, and identifying, with the processor, a second structure with a low pulsatility as the vein. In a fifth example of the method optionally including one or more of the first through fourth examples, adjusting the at least one imaging parameter responsive to the automatic identification of the artery and the vein comprises adjusting, with a processor, a steering angle of a color flow beam with respect to a B-mode imaging plane. In a sixth example of the method optionally including one or more of the first through fifth examples, adjusting the at least one imaging parameter responsive to the automatic identification of the artery and the vein comprises automatically centering, with a processor, a color flow region of interest within the artery or the vein. In a seventh example of the method optionally including one or more of the first through sixth examples, adjusting the at least one imaging parameter responsive to the automatic identification of the artery and the vein comprises automatically centering, with a processor, a pulsed wave cursor on the artery or the vein. In an eighth example of the method optionally including one or more of the first through seventh examples, adjusting the at least one imaging parameter responsive to the automatic identification of the artery and the vein comprises automatically adjusting, with a processor, a Doppler angle relative to the artery or the vein. In a ninth example of the method optionally including one or more of the first through eighth examples, the method further comprises displaying, via a display device, the color flow image, acquiring an updated color flow image with the adjustments to the at least one parameter, and displaying, via the display device, the updated color flow image.

In another embodiment, a method comprises receiving a selection of an imaging application, acquiring a color flow image according to the selected imaging application, automatically distinguishing an artery from a vein adjacent to the artery in the color flow image, and automatically positioning a display of a pulsed wave cursor on the artery or the vein in the color flow image according to the selected imaging application.

In a first example of the method, acquiring a color flow image according to the selected imaging application comprises acquiring the color flow image with a first pulsed repetition frequency responsive to the selected imaging application comprising a venous imaging application. In a second example of the method optionally including the first example, automatically distinguishing the artery from the vein comprises measuring, with a processor, variance in Doppler shifts within the color flow image, labeling, with the processor, a region exhibiting high variance as the artery, and labeling, with the processor, another region exhibiting low variance as the vein. In a third example of the method optionally including one or more of the first and second examples, automatically positioning the display of the pulsed wave cursor on the artery or the vein in the color flow image according to the selected imaging application comprises automatically positioning, with a processor, the display of the pulsed wave cursor on the vein in the color flow image. In a fourth example of the method optionally including one or more of the first through third examples, acquiring the color flow image according to the selected imaging application comprises acquiring the color flow image with a second pulsed repetition frequency responsive to the selected imaging application comprising an arterial imaging application, the second pulsed repetition frequency higher than the first pulsed repetition frequency. In a fifth example of the method optionally including one or more of the first through fourth examples, automatically distinguishing the artery from the vein comprises one of segmenting, with a processor, structures according to opposing flow directions and labeling, with the processor, the segmented structures as the artery and the vein, or measuring, with the processor, pulsatility in the color flow image and identifying, with the processor, regions of high pulsatility as the artery and regions of low pulsatility as the vein. In a sixth example of the method optionally including one or more of the first through fifth examples, the method further comprises adjusting imaging parameters based on the automatic positioning of the pulsed wave cursor, acquiring an updated color flow image with the adjusted imaging parameters, and displaying, via a display device, the updated color flow image.

In yet another embodiment, a system comprises an ultrasound probe, a user interface configured to receive input from an operator of the system, and a processor configured with instructions in non-transitory memory that when executed cause the processor to: receive, via the user interface, a selection of an imaging application; acquire, with the ultrasound probe, a color flow image according to the selected imaging application; identify an artery and a vein adjacent to the artery within the color flow image; and adjust one or more of a steering angle, a Doppler angle, and a position of a Doppler sample gate according to the identification of the artery and the vein.

In a first example of the system, the system further comprises a display device, wherein the processor is further configured with instructions in non-transitory memory that when executed cause the processor to display, via the display device, a cursor overlaid on the color flow image, and automatically position the cursor within the identified artery or the identified vein according to the selected imaging application. In a second example of the system optionally including the first example, the processor is further configured with instructions in non-transitory memory that when executed cause the processor to measure variance in Doppler shifts in the color flow image, wherein identifying the artery and the vein comprises labeling a structure with high variance as the artery and labeling a structure with low variance as the vein. In a third example of the system optionally including one or more of the first and second examples, the processor is further configured with instructions in non-transitory memory that when executed causes the processor to measure pulsatility in the color flow image, wherein identifying the artery and the vein comprises labeling a structure with high pulsatility as the artery and labeling a structure with low pulsatility as the vein.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
receiving selection of a venous imaging application via a user interface;
responsive to receiving the selection of the venous imaging application,
acquiring a color flow image that comprises an aliasing portion;
automatically identifying an artery and a vein within the color flow image based on the aliasing portion, wherein the vein is in contact with an other blood vessel, wherein the artery is automatically differentiated from the vein based on a processor identifying the aliasing portion, and wherein the artery is automatically identified by the processor as corresponding to the aliasing portion; and
adjusting at least one imaging parameter responsive to the automatic identification of the artery and the vein using the aliasing portion, wherein adjusting the at least one imaging parameter includes:
via the processor,
both automatically positioning a color flow region of interest (ROI) on the vein and automatically positioning a pulsed wave (PW) cursor on the vein responsive to a condition despite the vein being in contact with the other blood vessel, wherein the condition includes both the venous imaging application being selected and the identification of the artery and the vein using the aliasing portion having been performed.

2. The method of claim 1, contact, wherein acquiring the color flow image in the venous imaging application comprises scanning a subject with a first pulse repetition frequency that is lower than a second pulse repetition frequency according to the selection of the venous imaging application, and wherein the color flow ROI establishes a color flow field of view for color flow imaging.

3. The method of claim 2, wherein automatically identifying the artery and the vein within the color flow image comprises, responsive to receiving the selection of the venous imaging application and acquiring the color flow image with the first pulse repetition frequency, and wherein the aliasing portion is detected by the processor measuring regions of high spatial or temporal variance in flow velocity or direction within the aliasing portion of the color flow image relative to other regions of the color flow image.

4. The method of claim 1, wherein automatically identifying the artery and the vein within the color flow image comprises, responsive to receiving a selection of an arterial imaging application and acquiring the color flow image with a second pulse repetition frequency, identifying, with the processor, a first structure with a first flow direction and a second structure with a second flow direction opposite the first flow direction in the color flow image, and labeling, with the processor, the first structure and the second structure respectively as the artery and the vein.

5. The method of claim 1, wherein automatically identifying the artery and the vein within the color flow image comprises, responsive to receiving a selection of an arterial imaging application and acquiring the color flow image with a second pulse repetition frequency, measuring, with the processor, pulsatility in the color flow image, identifying, with the processor, a first structure with a high pulsatility as the artery, and identifying, with the processor, a second structure with a low pulsatility as the vein.

6. The method of claim 1, wherein adjusting the at least one imaging parameter responsive to the automatic identification of the artery and the vein comprises automatically adjusting, with the processor, a steering angle of a color flow beam with respect to a B-mode imaging plane.

7. The method of claim 1, wherein adjusting the at least one imaging parameter responsive to the automatic identification of the artery and the vein comprises one or more of automatically centering, with the processor, a color flow region of interest within the artery or the vein, and automatically centering, with the processor, a pulsed wave cursor on the artery or the vein.

8. The method of claim 1, wherein adjusting the at least one imaging parameter responsive to the automatic identification of the artery and the vein comprises automatically adjusting, with the processor, a Doppler angle relative to the artery or the vein to align with a vessel of interest, wherein the vessel of interest is the vein in the venous imaging application, and wherein the vessel of interest is the artery in an arterial imaging application.

9. The method of claim 1, further comprising:
displaying, via a display device, the color flow image;
acquiring an updated color flow image with the adjustments to the at least one parameter; and
displaying, via the display device, the updated color flow image.

10. The method of claim 1, wherein automatically positioning the color flow ROI on the vein and automatically positioning the PW cursor on the vein includes:
centering the color flow ROI on a point selected within the vein, and
centering the PW cursor on the point selected within the vein,
wherein centering the PW cursor on the point selected within the vein includes centering a Doppler range gate of the PW cursor on the selected point within the vein, a size of the Doppler range gate visualized in the PW cursor by a distance between a top and bottom graphic, and
wherein adjusting the at least one imaging parameter further includes, after automatically positioning the color flow ROI and the PW cursor on the vein, acquiring an updated color flow image with the color flow ROI and the PW cursor on the vein, and displaying the updated color flow image.

11. The method of claim 1, wherein automatically positioning the color flow ROI on the vein and automatically positioning the PW cursor on the vein includes centering the color flow ROI and the PW cursor on the vein responsive to the condition.

12. A method, comprising:
receiving a user selection of a venous imaging application via a user interface;
responsive to receiving the user selection of the venous imaging application,
acquiring a color flow image according to the venous imaging application that comprises an aliasing portion;
via a processor, using the aliasing portion to automatically distinguish an artery from a vein adjacent to the artery in the color flow image, wherein the artery is automatically identified by the processor as corresponding to the aliasing portion, wherein the vein is in contact with the artery in the acquired color flow image; and
via the processor, both automatically positioning a color flow region of interest (ROI) on the vein and a display of a pulsed wave cursor on the vein in the color flow image responsive to a condition, despite the vein being in contact with the artery in the acquired color flow image, wherein the condition includes both the selected imaging application being the venous imaging application and the identification of the artery and the vein using the aliasing portion having been performed.

13. The method of claim 12, wherein the vein is further in contact with another blood vessel, wherein automatically distinguishing the artery from the vein in the color flow image comprises detecting the aliasing portion by measuring, with the processor, a variance in Doppler shifts within the aliasing portion of the color flow image that is high relative to a region of the color flow image exhibiting low variance, labeling, with the processor, the aliasing portion detected by the processor as the artery, and labeling, with the processor, the region exhibiting low variance as the vein.

14. The method of claim 12, wherein automatically positioning the color flow ROI on the vein and automatically positioning the pulsed wave cursor on the vein in the color flow image includes automatically centering the color flow ROI and the pulsed wave cursor on the vein, with the processor, in the color flow image,
wherein the color flow ROI establishes a color flow field of view for color flow imaging,
wherein the pulsed wave cursor includes a Doppler beam cursor, an upper Doppler gate graphic, a lower Doppler gate, and a vessel slope cursor indicating a flow axis.

15. The method of claim 12, wherein acquiring a further color flow image according to a different selected imaging application comprises acquiring the further color flow image with a second pulsed repetition frequency responsive to the selected imaging application comprising an arterial imaging application, the second pulsed repetition frequency higher than a first pulsed repetition frequency of the venous imaging application.

16. The method of claim 15, wherein automatically distinguishing the artery from the vein in the further color flow image comprises one of segmenting, with the processor, structures according to opposing flow directions and labeling, with the processor, the segmented structures as the artery and the vein, or measuring, with the processor, pulsatility in the further color flow image and identifying, with the processor, regions of high pulsatility as the artery and regions of low pulsatility as the vein.

17. The method of claim 12, further comprising adjusting imaging parameters based on the automatic positioning of the pulsed wave cursor, acquiring an updated color flow image with the adjusted imaging parameters, and displaying, via a display device, the updated color flow image.

18. A system, comprising:
an ultrasound probe;
a user interface configured to receive input from an operator of the system; and
a processor configured with instructions in non-transitory memory that when executed cause the processor to:
receive, via the user interface, a selection of a venous imaging application or an arterial imaging application; and
responsive to the selection of the venous imaging application,
acquire, with the ultrasound probe, a color flow image according to the venous imaging application that includes an aliasing portion,
automatically identify an artery and a vein adjacent to the artery, wherein the aliasing portion within the color flow image acquired according to the venous imaging application is used to differentiate the artery from the vein, the artery identified as corresponding to the aliasing portion, wherein the vein is in contact with the artery in the acquired color flow image, and both automatically adjust a steering angle to position a region of interest (ROI) of the color flow image on the vein and automatically position a pulsed wave cursor on the vein responsive to a condition, despite the vein being in contact with the artery in the acquired color flow image, wherein the condition includes both the venous imaging application being selected and the identification of the artery and the vein within the color flow image having been acquired according to the venous imaging application using the aliasing portion.

19. The system of claim 18, further comprising a display device, wherein the processor is further configured with instructions in non-transitory memory that when executed cause the processor to:

responsive to the selection of the arterial imaging application, acquire, with the ultrasound probe, a color flow image according to the arterial imaging application,

identify an artery and a vein adjacent to the artery within the color flow image acquired according to the arterial imaging application based on flow direction, and adjust one or more of the steering angle, a Doppler angle, and a position of a Doppler sample gate according to the identification of the artery and the vein within the color flow image acquired according to the arterial imaging application.

20. The system of claim 18, wherein the processor is further configured with instructions in non-transitory memory that when executed cause the processor to measure variance in Doppler shifts in the color flow image, wherein identifying the artery and the vein comprises labeling a first structure with high variance at the aliasing portion as the artery and labeling a second structure with low variance as the vein.

21. The system of claim 18, wherein the vein is in contact with another blood vessel, wherein the steering angle is an angle between a color flow beam and a longitudinal axis of the ultrasound probe, and wherein the steering angle is automatically adjusted via the processor to steer the color flow beam and adjust a Doppler angle, the Doppler angle adjusted by adjusting a vessel slope cursor to align with a flow direction of blood within the vein.

* * * * *